United States Patent
Matsui

(10) Patent No.: US 6,957,095 B2
(45) Date of Patent: Oct. 18, 2005

(54) IMAGING SYSTEM FOR MEDICAL DIAGNOSIS

(75) Inventor: Susumu Matsui, Tochigi-ken (JP)

(73) Assignee: Kabushiki Kaisha Toshiba, Tokyo (JP)

( * ) Notice: Subject to any disclaimer, the term of this patent is extended or adjusted under 35 U.S.C. 154(b) by 0 days.

(21) Appl. No.: 10/263,961

(22) Filed: Oct. 4, 2002

(65) Prior Publication Data

US 2003/0069503 A1 Apr. 10, 2003

(30) Foreign Application Priority Data

Oct. 4, 2001 (JP) ........................................ 2001-308910

(51) Int. Cl.[7] .............................. A61B 5/05; A61B 8/08
(52) U.S. Cl. ...................................... 600/407; 600/443
(58) Field of Search ................................ 600/407, 409, 600/443, 447, 437; 345/581, 595, 762; 706/45–48, 55

(56) References Cited

U.S. PATENT DOCUMENTS

| | | | | |
|---|---|---|---|---|
| 4,905,163 A | * | 2/1990 | Garber et al. ................ | 706/55 |
| 5,235,510 A | * | 8/1993 | Yamada et al. ............. | 600/300 |
| 5,779,634 A | * | 7/1998 | Ema et al. ................... | 600/407 |
| 5,938,607 A | * | 8/1999 | Jago et al. ................... | 600/437 |
| 5,956,707 A | * | 9/1999 | Chu .............................. | 707/3 |
| 6,210,327 B1 | * | 4/2001 | Brackett et al. ............. | 600/437 |
| 6,323,869 B1 | * | 11/2001 | Kohm et al. ................ | 345/581 |
| 6,458,081 B1 | | 10/2002 | Matsui et al. | |
| 6,509,914 B1 | * | 1/2003 | Babula et al. .............. | 345/762 |
| 6,772,148 B2 | * | 8/2004 | Baclawski .................... | 707/3 |

FOREIGN PATENT DOCUMENTS

| | | |
|---|---|---|
| JP | 8-187244 | 7/1996 |
| JP | 2000-231429 | 8/2000 |
| JP | 2001-137237 | 5/2001 |

* cited by examiner

*Primary Examiner*—Francis J. Jaworski
(74) *Attorney, Agent, or Firm*—Oblon, Spivak, McClelland, Maier & Neustadt, P.C.

(57) ABSTRACT

An apparatus for medical diagnostic imaging may include a database that relates help information with multiple types of attribute values and stores this information; an operations state acquisition part that acquires the attribute values that expresses the current operational status of the medical diagnostic imaging apparatus; a search part that searches the knowledge database, based on the attribute values; and a display that displays help information or a list of help information, based on the search results of the search part. As the present invention searches for and displays help information according to the operational status of the apparatus for medical diagnostic imaging, it is possible to provide the operator with help information suitable for a diagnosis currently being made.

13 Claims, 13 Drawing Sheets

EXAMPLES OF ATTRIBUTE INFORMATION (ULTRASOUND DIAGNOSTIC APPARATUS)

| ATTRIBUTE NAME | VALUES (CODES) | |
|---|---|---|
| TITLE | VOLUME MEASUREMENT METHOD OF THE LEFT VENTRICLE | ⇒ TITLE FOR DISPLAY |
| PROGRAM | DISTANCE MEASUREMENT | ⇒ EXECUTED PROGRAM |
| PROBE | SECTOR SCAN | ⇒ APPARATUS CONTROL DISPLAY STATUS |
| IMAGING MODE | D-MODE | |
| TRANSMITTING FREQUENCY | 3.5MHz | |
| EXPANSION OF IMAGE | 2 TIMES | |
| DIVISION OF IMAGE | * | |
| HELP INFORMATION FILE | 123123 | |

FIG. 5

EXAMPLES OF ATTRIBUTE INFORMATION (NUCLEAR MEDICINE APPARATUS)

| ATTRIBUTE NAME | VALUES (CODES) | |
|---|---|---|
| TITLE | VOLUME MEASUREMENT METHOD OF THE LEFT VENTRICLE | ⇒ TITLE FOR DISPLAY |
| PROGRAM | QGS | ⇒ EXECUTED PROGRAM |
| ACQUISITION MODE | SPECT SYNCHRONIZED WITH CARDIOGRAPH | ⇒ APPARATUS CONTROL DISPLAY STATUS |
| HELP INFORMATION FILE | 1234 | |

FIG. 6

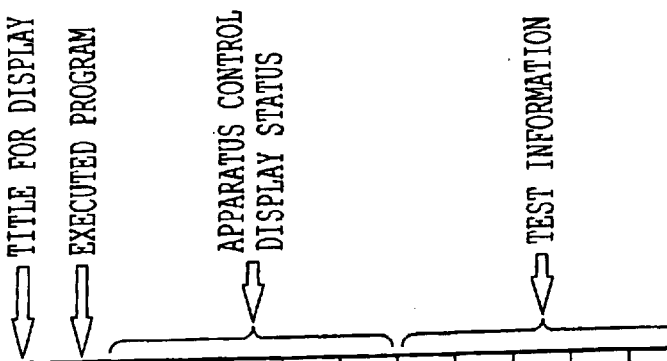

EXAMPLES OF ATTRIBUTE INFORMATION (ULTRASOUND DIAGNOSTIC APPARATUS)

| ATTRIBUTE NAME | VALUES (CODES) | |
|---|---|---|
| TITLE | VOLUME MEASUREMENT METHOD OF THE LEFT VENTRICLE | ⇒ TITLE FOR DISPLAY |
| PROGRAM | DISTANCE MEASUREMENT | ⇒ EXECUTED PROGRAM |
| PROBE | SECTOR SCAN | ⇖ |
| IMAGING MODE | D-MODE | |
| TRANSMITTING FREQUENCY | 3.5MHz | APPARATUS CONTROL DISPLAY STATUS |
| EXPANSION OF IMAGE | 2 TIMES | |
| DIVISION OF IMAGE | * | ⇙ |
| CONTRAST AGENT | LEVOVIST- | |
| TEST NAME | ADULT HEART | ⇖ |
| TEST REGION | HEART | |
| ADDITIONAL INFORMATION | SHORT AXIS | TEST INFORMATION |
| TEST ORDER | CARDIO-FUNCTION TEST | |
| HELP INFORMATION FILE | 9873 | ⇙ |

FIG.8

EXAMPLES OF ATTRIBUTE INFORMATION (NUCLEAR MEDICINE APPARATUS)

| ATTRIBUTE NAME | VALUES (CODES) | |
|---|---|---|
| TITLE | VOLUME MEASUREMENT METHOD OF THE LEFT VENTRICLE | ⇒ TITLE FOR DISPLAY |
| PROGRAM | QGS | ⇒ EXECUTED PROGRAM |
| ACQUISITION MODE | SPECT SYNCHRONIZED WITH CARDIOGRAPH | ⇒ APPARATUS CONTROL DISPLAY STATUS |
| TEST NAME | QGS | ⇒ TEST INFORMATION |
| MEDICINE | THULIUM CHLORIDE | |
| RADIOISOTOPE | 201-TI | |
| CASE | INFARCTION OF THE LEFT VENTRICLE FRONT WALL | |
| TEST ORDER | CARDIO-FUNCTION TEST | |
| HELP INFORMATION FILE | 1234 | |

FIG. 9

TRANSFORMATION TABLE

| TRANSFORMED ATTRIBUTE VALUES (CODES) | ORIGINAL ATTRIBUTE VALUES (CODES) |
|---|---|
| TEST REGION = HEART | TEST REGION = HEART |
| PROGRAM = DISTANCE MEASUREMENT OF HEART | PROGRAM = DISTANCE MEASUREMENT & TEST REGION = HEART |
| PROGRAM = AACT | PROGRAM = ACT |
| ATTRIBUTE VALUES Z = ACTIVE | TEST REGION = ABDOMEN & IMAGING MODE = B MODE & PROGRAM = DISTANCE MEASUREMENT & DIVISION OF IMAGE = 2 |
| ------- | ------- |

FIG. 15

IMAGING SYSTEM FOR MEDICAL DIAGNOSIS

CROSS-REFERENCE TO RELATED APPLICATIONS

This application is based upon and claims the benefit of priority to the prior Japanese Patent Application No. 2001-308910, filed Oct. 4, 2001, the entire contents of which are incorporated herein by reference.

BACKGROUND OF THE INVENTION

1. Field of the Invention

The present invention relates to an imaging system for medical diagnosis that displays the medical image data of an ultrasound diagnostic apparatus, an X-ray diagnostic apparatus, an endoscopic apparatus, an X-ray computed tomography apparatus, a magnetic resonance imaging apparatus, a nuclear medicine apparatus, and the like. In particular, the invention relates to an improved display function for help information.

2. Description of the Related Art

Because methods of operating imaging systems for medical diagnosis are extremely complex and different manufacturers often have different operating procedures, an operator frequently needs information about how to operate a system during its operation.

Because of this, in ultrasound diagnostic apparatus, X-ray diagnostic apparatus, endoscopic apparatus, X-ray computed tomography apparatus, magnetic resonance imaging apparatus, and nuclear medicine apparatus of the prior art, information about methods of operation are displayed as help information to provide support to the operator.

In the prior art, there are two primary methods of searching for help information, one of which involves the entry of a search keyword (or keywords) and the other involving the selection of classes of pre-determined operational circumstances, which are presented as units of ten, arranged in a tree-form. However, when the amount of help information accumulated is large, the operator must sort through large quantities of help information until the desired help information is found and this places a burden on the operator.

Previously known methods of displaying help information include the location of a help button on various operation screens with the necessary help information is displayed on the operating screens. However, this method necessitates the installation of a help button on each operating screen and the provision of help information corresponding to each of these help buttons. Because of this, when operating screens are designed, it is necessary to take into account how help information will be dealt with on each screen, which imposes a burden on the programmer. It is generally difficult to produce a system that users find satisfactory.

Additionally, the prior art help information shown concerns only the operation of the apparatus. In some cases, however, it is desirable to have clinical information about the study region, images of previous clinical examples and/or cautions for the study. In the prior art, such information must be found from books or other literature or from a separate personal computer, or the like.

BRIEF SUMMARY OF THE INVENTION

In one aspect of the present invention, an apparatus for medical diagnostic imaging having a database, an operations state acquisition part, a search part, and a display is provided.

Since help information is searched for and displayed according to the operational status of the imaging apparatus for medical diagnosis, it is possible to provide the operator with help information appropriate to the study currently being performed.

Additional advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE DRAWINGS

The accompanying drawings, which are interpreted in and constitute a part of the specification, illustrate presently preferred embodiments of the invention, and together with the general description given above and the detailed description of the preferred embodiments given below, serve to explain the principles of the invention.

FIG. 5 is an example of the attribute information of an ultrasound diagnostic apparatus according to the first embodiment.

FIG. 6 is an example of the attribute information of a nuclear medicine apparatus according to an embodiment of the invention.

FIG. 8 is an example of the attribute information of an ultrasound diagnostic apparatus according to the second embodiment.

FIG. 9 is an example of the attribute information of a nuclear medicine apparatus according to the third embodiment.

FIG. 15 is an example of a specification transformation table for the fifth embodiment.

DETAILED DESCRIPTION OF THE INVENTION

Below, embodiments of the imaging system for medical diagnosis according to the invention are described with reference to the figures. The descriptions below take an ultrasound diagnostic apparatus and a nuclear medicine apparatus as examples, but are not limited thereto.

First Embodiment

The first embodiment of an ultrasound diagnostic apparatus changes the content of the help information supplied to the operator according to the image gathering mode of the ultrasound diagnostic apparatus, the image gathering conditions, the type of measurement program being executed, image display conditions and other current operating conditions of the apparatus. Because of this, the operator can easily refer to the necessary help information.

Figure 1:
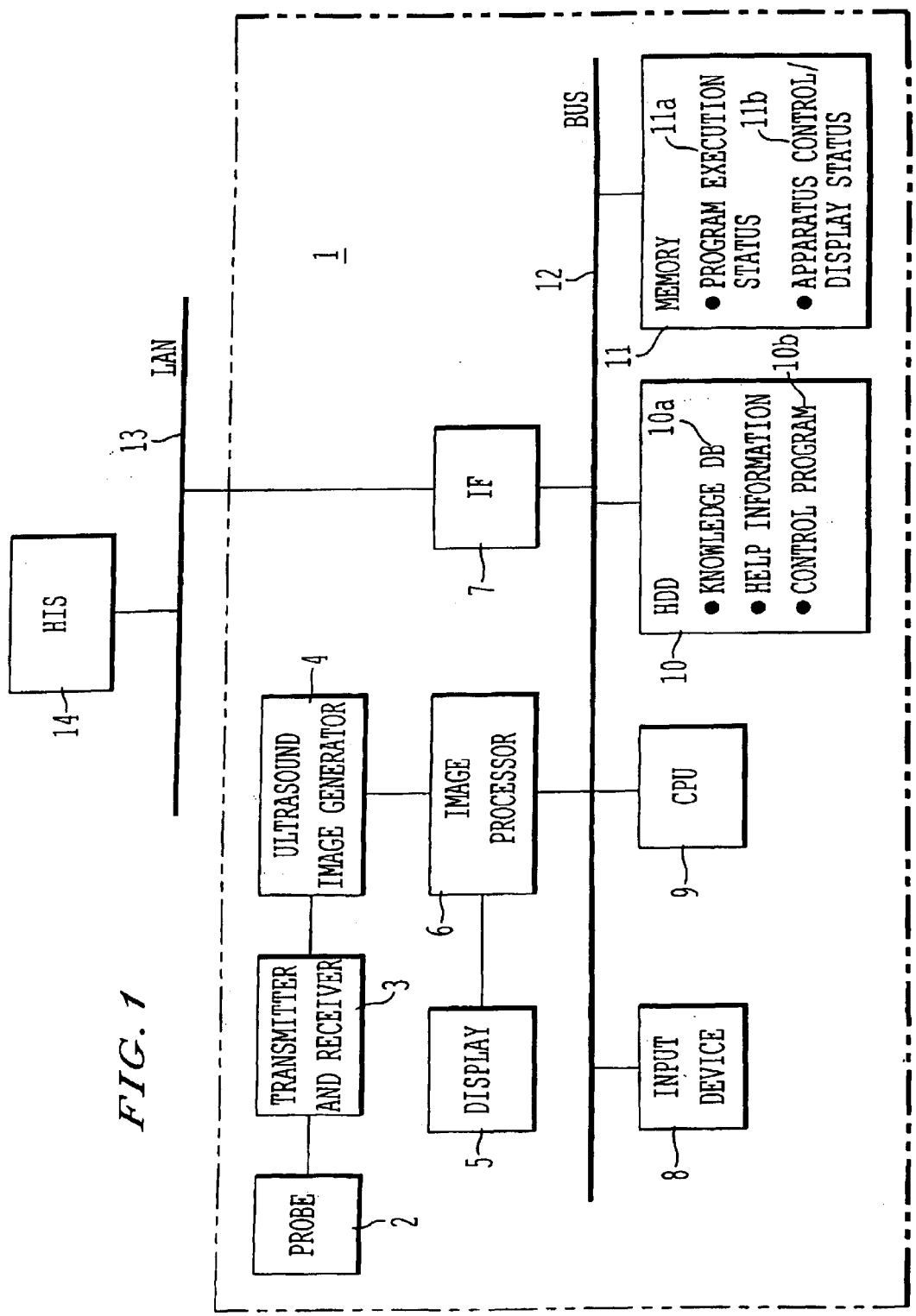
FIG. 1 is a block diagram showing an ultrasound diagnostic apparatus according to the first embodiment.

FIG. 1 is a structural diagram of an ultrasound diagnostic apparatus according to the first embodiment. The ultrasound diagnostic apparatus 1 has an ultrasonic probe 2, transmitter and receiver 3, ultrasound image generator 4, display 5, image processor 6, IF (network interface) 7, input device 8, CPU (central processing unit) 9, HDD (hard disk device) 10, memory 11, and bus 12. Ultrasonic probe 2 sends and receives ultrasonic waves to and from the object being studied. The transmitter and receiver 3, ultrasound image generator 4, and image processor 6 generate ultrasound images based on scan setting information and image generation conditions. Transmitter and receiver 3 generates signals to drive the ultrasound probe 2 and also processes signals received by ultrasonic probe 2. Transmitter and receiver 3 gradually changes the direction of the ultrasonic beam to carry out scans of sections of the body, thereby obtaining ultrasound images. Ultrasound image generator 4 generates ultrasound images on the basis of the ultrasonic echo signals output from transmitter and receiver 3. Ultrasound image generator 4 carries out the necessary processing of the signals, according to the image generation mode, including B mode, CFM mode and Doppler mode. Image processor 6 synthesizes alphanumeric characters, graphics, and the ultrasound images generated by the ultrasound image generator 4, generates display images, and displays the display images in display 5.

The IF 7, which is for connection to a LAN (local area network) 13 of the hospital, is connected via the LAN 13 to the HIS (hospital information system) 14. HIS 14 sends order information concerning the study to the ultrasound diagnostic apparatus 1 via the LAN 13. The order information, which includes information on an order for a study made by the responsible doctor, may include requests for a liver function study, stress echo study, cardiac echo study and renal function study, as well as other similar requests.

Input device 8, which is used by the operator for inputting, is a manually operated device such as an operating panel, mouse, or the like. CPU 9 controls the parts on the basis of programs and data stored in HDD 10 and memory 11. HDD is a large-capacity electromagnetic memory computer-readable device, which stores files describing help information, knowledge database 10a having attribute information related to the help information, and control program 10b, etc. Memory 11, a semiconductor computer-readable memory element, stores the program execution status 11a and the apparatus control display status 11b. Bus 12 is a data communication circuit that transmits information between the above described elements.

Figure 2:
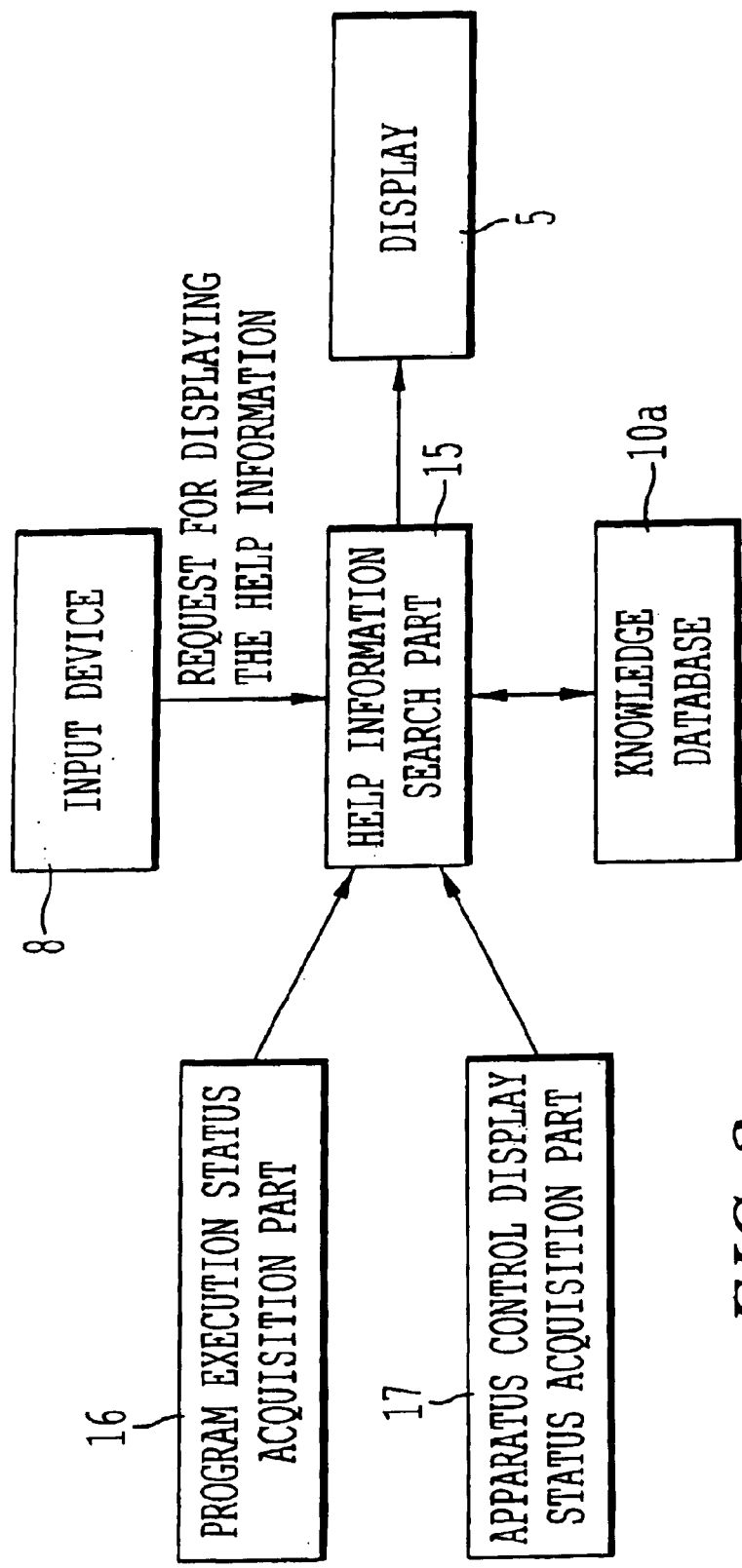
FIG. 2 is an explanatory diagram for the operations of an ultrasound diagnostic apparatus according to the first embodiment.

FIG. 2 is an explanatory diagram for the operations of an ultrasound diagnostic apparatus according to the first embodiment. Help information search part 15 plays a central role of help information display function. Help information search part 15, program execution status acquisition part 16, apparatus control display status acquisition part 17 are effectuated through the execution of, respectively, a help information display program, a program execution status acquisition programs and an apparatus control display status acquisition program by the CPU 9.

When the help information search part 15 receives a help information display request input from the input device 8, the information 11a of programs being executed by the ultrasound diagnostic apparatus 1 and the apparatus control display status 11b is acquired from the program execution status acquisition part 16 and apparatus control display acquisition part 17. The help information search part 15 searches for the attribute information (which typically includes a name and value for each attribute) in the knowledge database 10a, with the program execution status 11a and apparatus control display status 11b as search conditions. The help information search part 15 selectively reads the help information file corresponding to the attribute information to which the search applies from the knowledge database 10a, and displays help information in display 5.

In addition to support information concerning methods of operating the apparatus, the multiple help information files contain clinical information about the study region, still or moving pictures of clinical examples, information about cautions for the study. The physicians conducting the study may obtain not only information about how to operate the apparatus, but also clinical knowledge and knowledge about the study.

When the operator inputs a help information display request via the input device 8, the program execution status 11a and apparatus control display status 11b are acquired at that time from the program execution status acquisition part 16 and the apparatus control display status acquisition part 17 and are sent to the help information search part 15.

Figure 3:
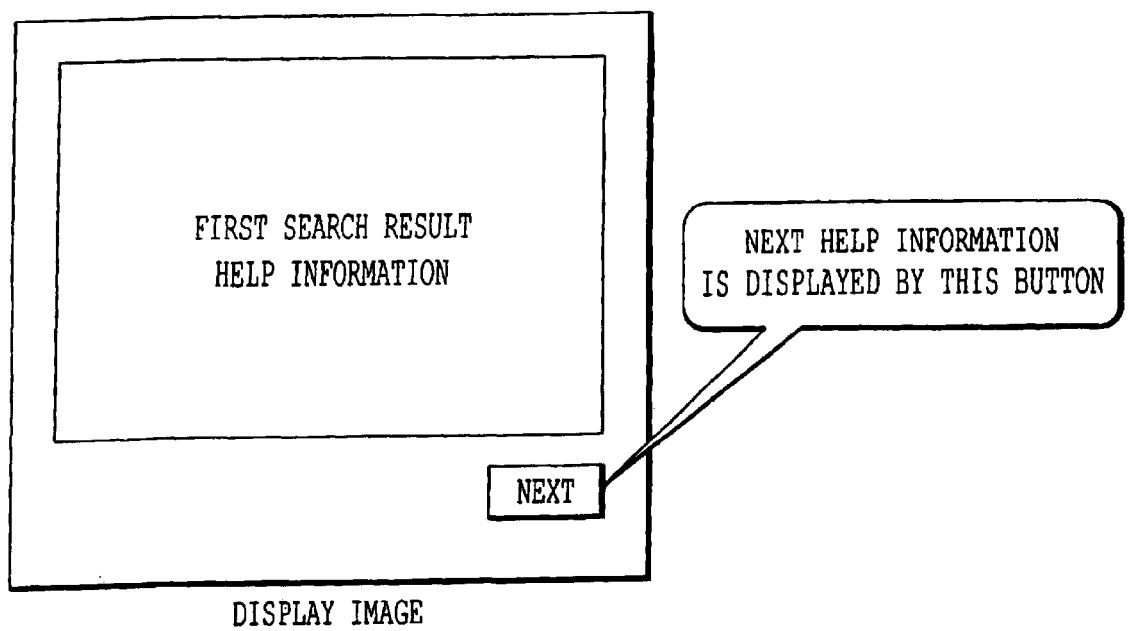
FIG. 3 is an example of a display screen for help information according to the first embodiment.

The help information search part 15 searches in the knowledge database 10a with the program execution status 11a and apparatus control display status 11b as search keys and the help information to which the relevant attribute value is related is displayed at the display 5. If there is more than one search result, the 'NEXT' button is displayed, as shown in FIG. 3, and the next help information is displayed in sequence each time this button is pressed. The default order in which these are displayed is the order of registration. The order may be changed dynamically according to reference history, so the help information file being displayed is shown in the top position. Also, a list based on the search results may be displayed as the help information and the operator may then freely select help information files from this list for display.

Figure 4:
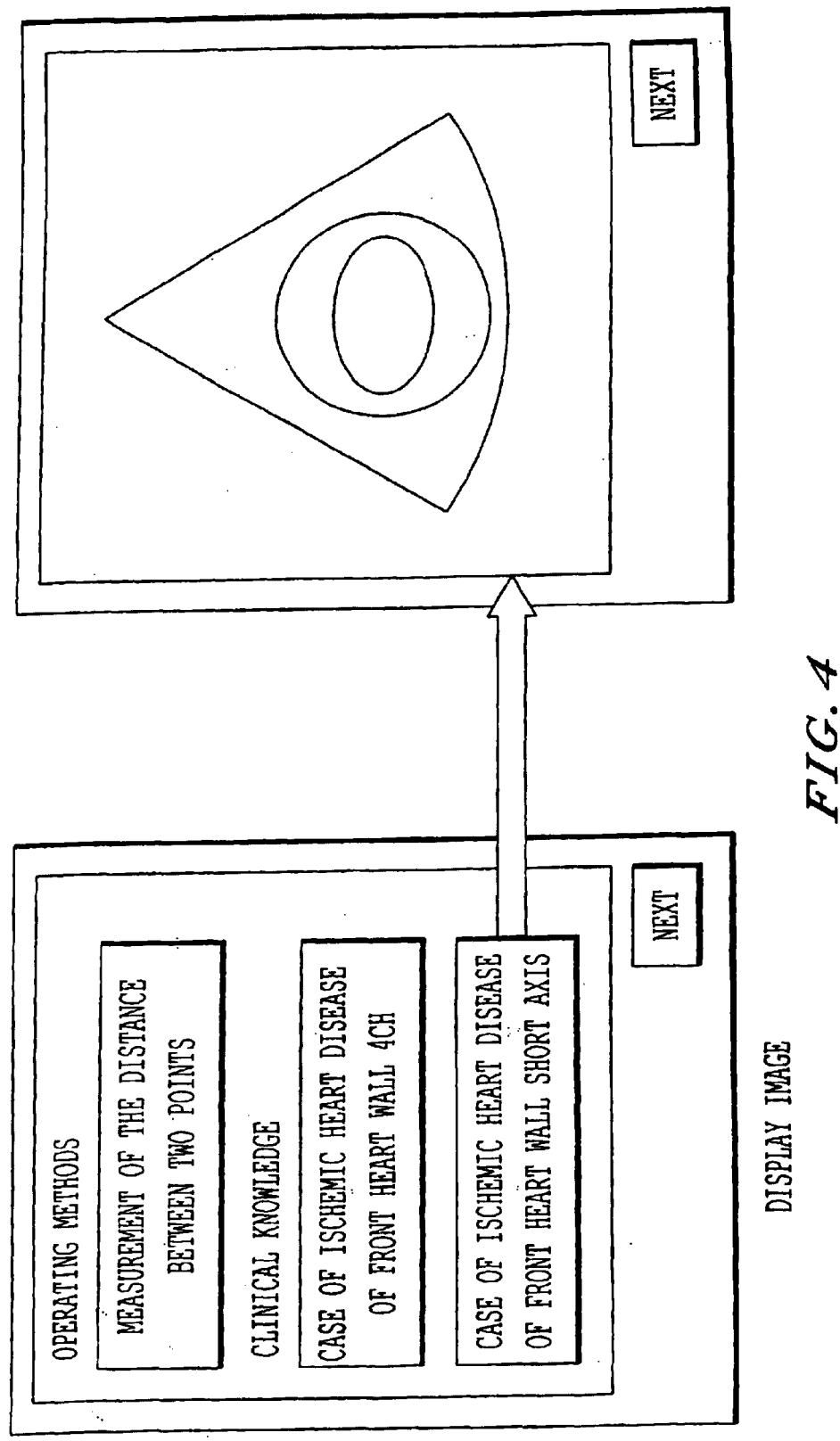
FIG. 4 is an example of another display screen for help information according to the first embodiment.

Additionally, as shown in FIG. 4, the multiple help information files may be classified into apparatus operation methods, clinical knowledge, exemplary clinical images, as well as other categories, with the titles of these displayed simultaneously as a list. The operator may be prompted to select from this list. If the operator does not require display of the apparatus operating methods but only the clinical knowledge and exemplary clinical images, it is possible to pre-set so that help information files concerning apparatus operation methods are excluded and only the clinical knowledge and exemplary clinical images are displayed. Direct images and the contents themselves may be displayed rather than the titles.

As is shown in the examples of attribute information of the ultrasound diagnostic apparatus shown in FIG. 5, titles of attribute information, attribute values (or codes) that express the execution status of the programs, and attribute values that express the control display status of the ultrasound diagnostic apparatus are stored as identifiers to specify the help information files in a relational knowledge database. The title of the first attribute information is used to display the search results on the screen. In this example, the title is in characters. If this were an image file title, an image could be displayed to the user instead of the character string.

The execution status of a program means, for example, a program name that specifies the program currently being executed by the operations of the operator. Programs usually installed in an ultrasound diagnostic apparatus include a patient registration program to register the patient name, a doctor registration program to register the doctor name, a study registration program, a distance measurement program for the measurement of the distance between points, an area and volume measurement program for the measurement of the area and volume of a region of concern, a cardiac function calculation program to calculate the left ventricular end-systolic (or diastolic) volume, a velocity measurement program, an annotation program to display comment on the medical image, an image file management program to record and search images, and a body mark program to display a graphical mark of a human body with the medical image. A subdivision of any of these programs may be specified as the program status; for example, the distance measurement program may be subdivided and the distance measurement start-point setting program section and/or distance measurement end-point setting program section may be specified.

The control status of the ultrasound diagnostic apparatus is information concerning scan settings and image generation conditions related to the generation (and gathering) of clinical image data and in this embodiment this includes the probe name (and scan method), the imaging mode of the apparatus (B mode, M mode, D (Doppler) mode, CFM (Color Flow Doppler) mode) and picture quality condition parameters (transmission frequency, focus point, depth of field, gain, etc.) currently in use. The display status includes enlarged display settings and screen division settings.

FIG. 6 shows an example of attribute information in a nuclear medicine apparatus in accordance with an embodiment of the invention. The knowledge database 10a stores identification codes to specify titles, program names, order information, gathering mode and help information files as attribute information. This information, which may include attribute values, related with the help information files, is stored as a searchable table. In this embodiment of a nuclear medicine apparatus, as shown in FIG. 6, a program name is QGS for a cardiac function study. In this embodiment of a nuclear medicine apparatus, the control status of the apparatus may be static collection, dynamic collection, ECG-synchronized collection, SPECT, continuous rotating SPECT and ECG-synchronized SPECT. The meaning of display status of the apparatus encompasses the presence or absence of enlarged display of clinical image data displayed in high-definition, the enlargement ratio of the clinical image data, and the screen division status.

These attribute values are set by predetermined combinations for each modality and attribute values corresponding to the various help information files are assigned when the file is registered. It is possible that an attribute values may be a specification code (e.g., the symbol *) as a wild card, which will establish the conditions for any value in the search. For example, in the case of FIG. 5, a wild card is assigned in relation to a split screen. The help information file is selected when another attribute applies to the requirement, without regard to the attribute values having a wild card, for example, whether there is no screen division or it is divided into two or divided into three.

If there are different types of diagnostic apparatus, it is easy to create a database by changing the attribute name and creating a new database. A database may be shared by all the diagnostic devices by defining a common attribute name for all of the diagnostic devices. For example, it is possible to prepare a general-use database, unaffected by differences in modality and manufacturer, by using a code and name defined by DICOM3.0 as the attribute name.

In the first embodiment, it is possible to supply the operator with help information appropriate to the circumstances of the diagnosis and thus to improve the operational characteristics of the apparatus. For example, it is possible to display additional special cautions for M mode when distance measurement is performed in this mode. It is possible to add special cautions regarding the probe in use and to provide finely detailed information of greater use to the operator by adding the display status to the search, for example, by displaying the status of the M-mode display in the left part of a screen divided into two.

Also, since this knowledge database 11a is not a program, additional registration is simple. Since additional registration may be carried out by the user, rather than just by the manufacturer, users may change the help information to suit themselves. In the prior art, supplying help information of such fine detail would necessitate the incorporation of information in the program itself. By contrast, in the method of this embodiment, display algorithms of basically the same level of fine detail may be supplied by setting the attribute value when the help information file is registered in the knowledge database 3. This means that there is no need to change the program. It is thus possible to provide a system with a more flexible expandability.

Second Embodiment

Figure 7:
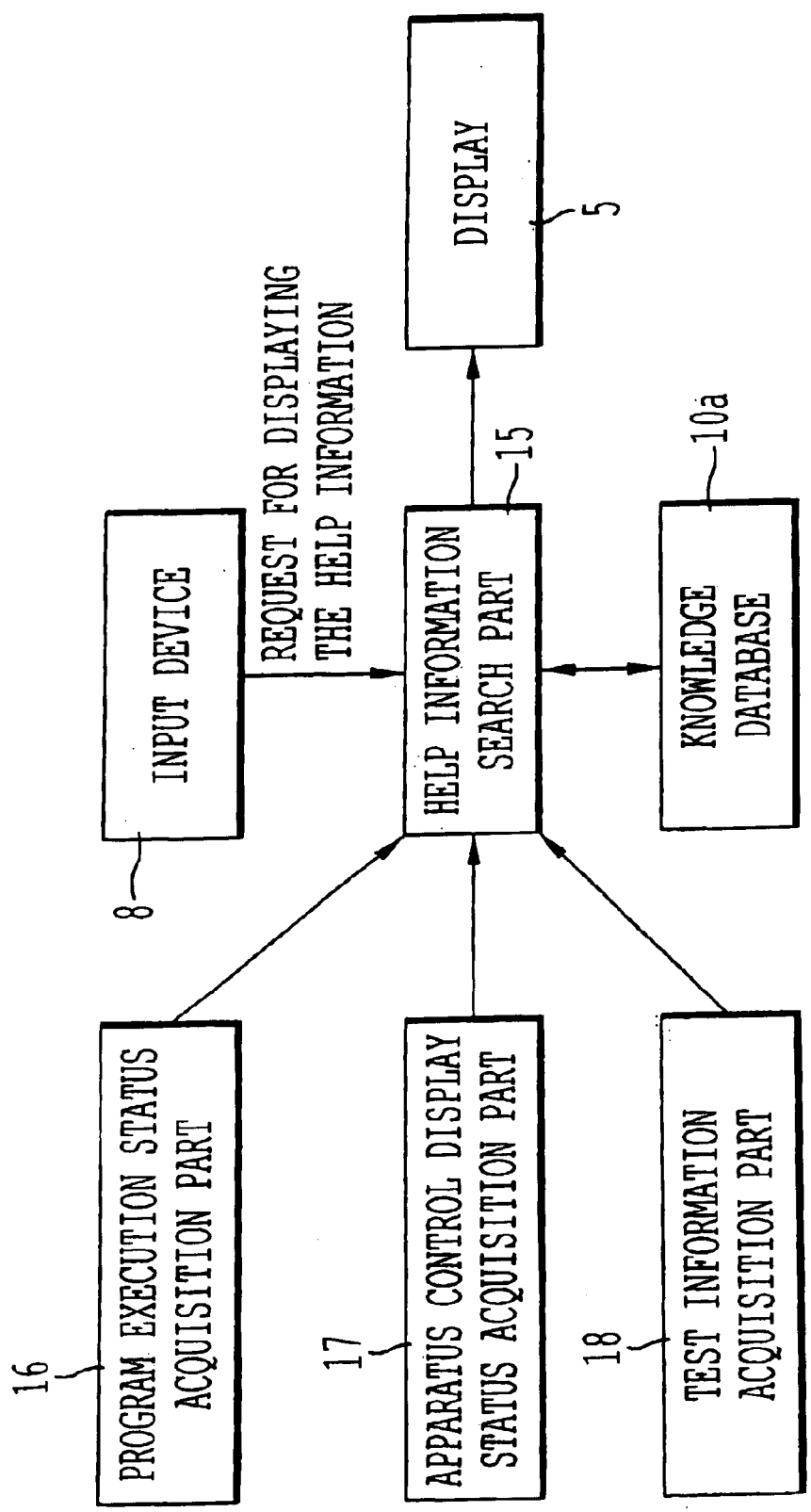
FIG. 7 is an explanatory diagram for the operations of an ultrasound diagnostic apparatus according to the second embodiment.

Below, the operations of the ultrasound diagnosis apparatus according to the second embodiment are described with reference to FIG. 7. Descriptions of those parts that are identical to the embodiment described above are omitted. The second embodiment is characterized in that it has a study information acquisition part 18. Study information acquisition part 18, which acquires study information 11c related to the content of the study, is effectuated by the execution by CPU 9 of a study information acquisition program.

FIG. 8 shows one example of the attribute information in this embodiment. This attribute information has a search table for attribute values related to program execution status 11a, apparatus control display status 11b and study information 11c. Study information 11c includes the type of contrast medium, the study name, the region on the body of the study, as well as additional information about the region and study order sent from HIS 14.

In the ultrasound diagnostic apparatus 1, before the start of the study, the study request information from the requesting department is referred, the purpose for which the study will be carried out is input from the input device 8, and the apparatus is set to the initial status that is optimum status for the study. For example, in the ultrasound diagnostic apparatus 1, the study information 11c includes information such as that the study is examining the abdomen or adult heart. Initial transmission frequency, focus location, and the like of the probe 2 are set using this information. Also, the study information 11c input from the input device 8 is stored in the memory 11. The study information acquisition part 18 reads the information in the memory 11 and acquires the study information 11c. The help information search part 15 searches for attribute information in the knowledge database 10a, based on the program execution status 11a, apparatus control display status 11b and study information 11c, and displays the files or lists extracted by this search.

FIG. 9 shows an example of the attribute information of the nuclear medicine apparatus according to an embodiment of the invention. In this embodiment, the study information 11c includes the study name, the name of the pharmaceutical products used, the radioisotope name, the case name, and order information. It is also possible to search for help information using this type of study information 11c, as in the ultrasound diagnostic apparatus described above.

Since, in the second embodiment, searches for help information may be made based on program status, the control and display status of the apparatus and study information, it is possible to display help information appropriate to the diagnosis circumstances. In particular, since the search is performed using study information, when help is provided, it is possible to extract suitable help information about clinical images and to provide descriptions of the operations necessary to obtain examples of clinical images when these are provided.

Third Embodiment

Figure 10:
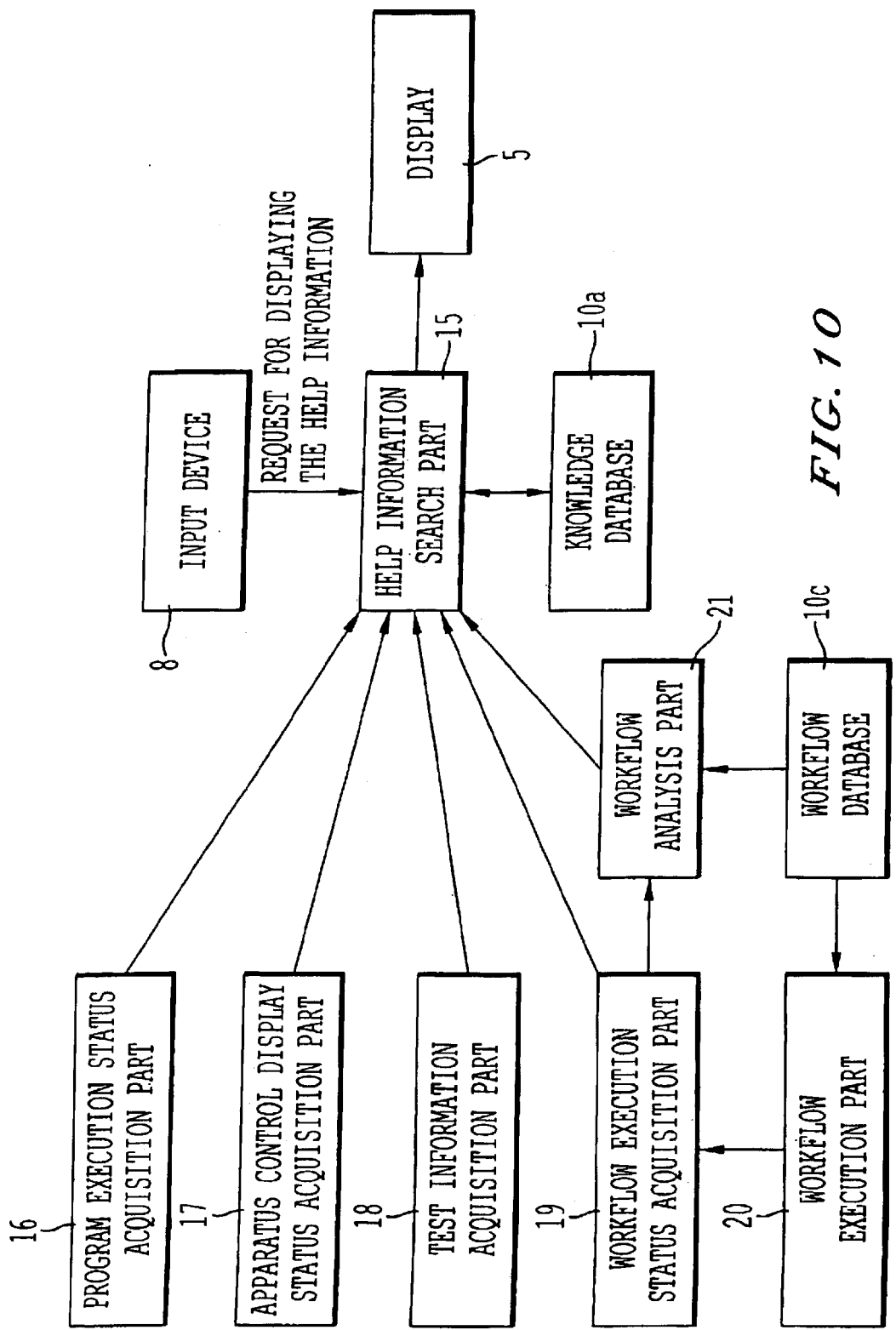
FIG. 10 is an explanatory diagram for the operations of an ultrasound diagnostic apparatus according to the third embodiment.
Figure 11:
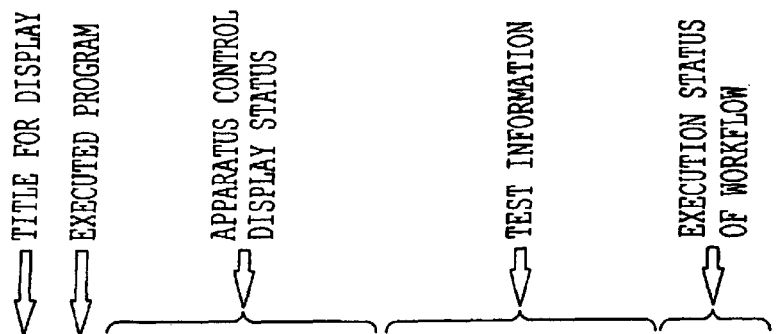
FIG. 11 is an example of the attribute information of an ultrasound diagnostic apparatus according to the third embodiment.
Figure 12:
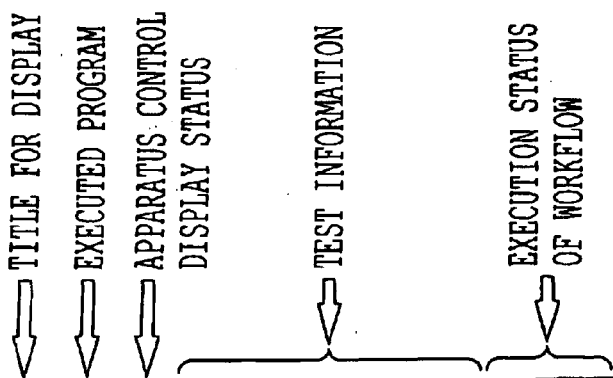
FIG. 12 is an example of the attribute information of a nuclear medicine apparatus according to the third embodiment.

Below the operations of the ultrasound diagnosis according to the third embodiment are described with reference to FIG. 10. Descriptions of those parts that correspond to those of the embodiments described above are omitted. The third embodiment selects help information for display according to the execution status of the study sequence (workflow) 11d.

The ultrasound diagnostic apparatus of embodiment 3 has workflow execution state acquisition part 19, workflow execution part 20, and workflow analysis part 21. A workflow database 10c is stored in HDD10. Workflow execution state acquisition part 19, workflow execution part 20, and workflow analysis part 21 are effectuated by, respectively, a workflow execution state acquisition program, workflow execution program, and workflow analysis program executed in the CPU 9.

Multiple types of workflows may be stored in the workflow database 10c. The workflow, which defines the execution order of multiple tasks, may be adapted to the workflow for, for example, liver function studies, stress echo studies, cardiac echo studies, or renal function studies. The tasks are related to the information that controls the operations of the ultrasound diagnostic apparatus. For example, these operations may include patient registration, imaging mode switching between, for example B mode and D mode, execution of measurement programs, and storage of study images.

For example, if the operator makes an input to the effect that a liver function study will be carried out, the workflow execution part 20 reads the workflow data file corresponding to a liver function study from the study workflow database. Then, the tasks defined by this workflow are executed in sequence. At this time, icons corresponding to the tasks are displayed in a row in the display 5. The operator can easily understand the entire study procedure by workflow and the progress study from these icons.

Workflow execution part 20 stores the name of the study sequence currently being executed and the study step information that defines the task in this study sequence that is currently being executed (this may include the task name and the identification information to define the task) as workflow execution state 11d in the memory 11. The workflow execution part 20 also transforms the operations of the ultrasound diagnostic apparatus, according to the content defined in the task, by changing the program execution status 11a, apparatus display status 11b, and study information 11c. The workflow acquisition part 19 acquires the execution state 11d of the workflow by reading the information in memory 11.

Workflow analysis part 21 reads the workflow corresponding to the workflow execution state 11d of the workflow from the study sequence database 10c and outputs the analysis result for the workflow. This analysis result is a fixed value based on the relationship with the processes contained in the preceding and succeeding tasks and the contents of the processes themselves. The result may be, for example, the number of executions of the same program in the workflow.

Figure 13:
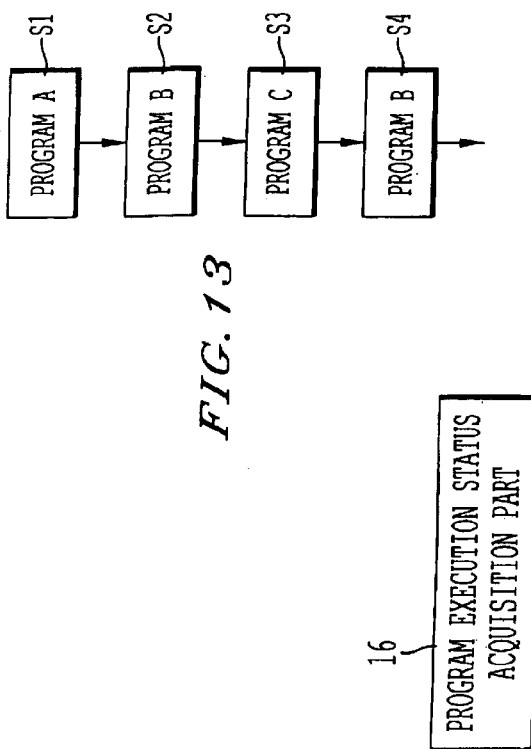
FIG. 13 is an example of the program execution sequence in the third embodiment.

FIG. 13 is an example of a workflow according to an embodiment of the invention. The example workflow is defined such the same program runs in task S2 and task S4. When task S2 is being executed, workflow analysis part outputs '1' as the number of executions of the same program in the workflow and if task S4 is being executed, it outputs '2'.

Along with the program execution status 11a, the apparatus control display status of the ultrasound diagnostic apparatus 11b, and study information 11c, the execution status of the workflow 11d and the analysis result for the workflow are also input into the help information search part 15. Help information search part 15 searches for help information that matches these attribute information and displays these in display 5. Also, attribute values corresponding to the analysis result of the workflow, the program execution status 11a, apparatus control display status of the ultrasound diagnosis apparatus 11b and study information 11c, the execution status of study sequence 11d and the analysis result of the study sequence are stored in the attribute information of the knowledge database 10a.

When the workflow analysis result is not used for a search, as in the study sequence shown in FIG. 13, if the same program B runs in both task S2 and task S4 and if the control display status 11b of the apparatus is exactly the same at the time, the help information displayed is the same at both task S2 and task S4. In this embodiment, as searching for help information is carried out based on information about the number of executions (for example, the first execution and second execution of program B), it is possible to display different help information at task S2 and task S4.

For example, in a cardiac study, it is common practice to carry out studies before and after applying an exercise load. In this kind of study sequence, since the first time that program B is executed is before the load, the help information shown at this time is pre-load information. Similarly, it is possible to display post-load information at the time of the second execution. It is thus possible to display different help information even during the execution of the same program by changing positions in the overall study sequence.

In the example described above, the number of executions is used as the analysis result but the value of the analysis result may be changed according to whether program A is executed before program B. In this case, it is easy to create a database in which the relationships with the preceding and succeeding programs are made to correspond with the analysis result values and the analysis result may be found based on this.

In the third embodiment, since searches for help information are based on the execution circumstances of the workflow, it is possible to provide appropriate help information to the operator. For example, it is possible to display help information corresponding to the name of the study sequence being executed.

Since help information searches are based on information about the task being executed, the help information displayed may be changed as the task moves. For example, when the task is on the short axis, it is possible to instantly display examples of clinical images of the short axis and also to display help information that is of benefit to the operator.

Also, as searches for help information are based on the analysis result of the task sequence, it is possible to change the help information displayed appropriately according to the position of the task in the task sequence, even when the task itself remains the same.

Fourth Embodiment

Figure 14:
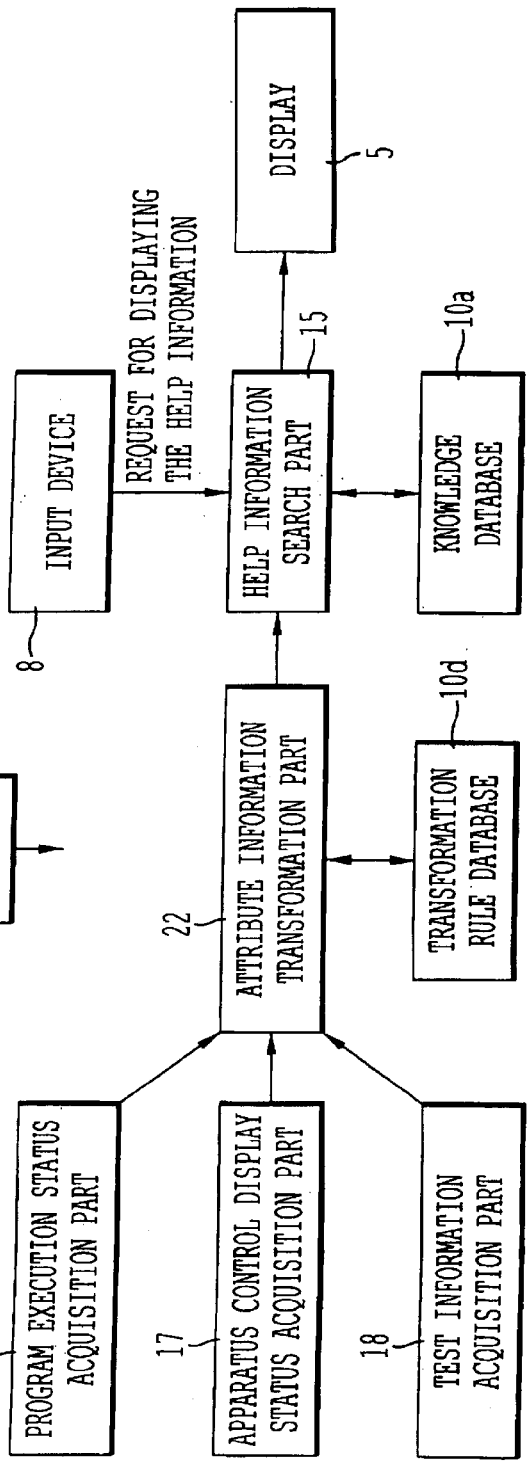
FIG. 14 is an explanatory diagram for the operations of an ultrasound diagnostic apparatus according to the fourth embodiment.

Below, the operations of the ultrasound diagnosis apparatus according to the fourth embodiment are described with reference to FIG. 14. Descriptions of those parts that correspond to the embodiments described above are omitted.

For knowledge database 11a, it is anticipated that there will be an increased quantity of attribute information due to repeated registration updates. When there is a change in an attribute value (even when, for example, the actual content is identical) and there is a change in the name of the study or the program, the task of correcting the attribute value of the help information file in the knowledge database 11a to the new attribute value to accord with this transformation can be great. In this embodiment, in place of this correction operation, the attribute information of the help information file in the knowledge database 11a retains the old attribute value, without any correction, and this attribute value is transformed to a new attribute value by the attribute information transformation part 22 to effectuate a search with the new attribute value.

In the first, second, and third embodiments described above, searches are performed using the program execution status 11a, the apparatus control display status 11b, and study information 11c and the execution status of the study sequence 11d unmodified. However, in the fourth embodiment these input attribute values are changed to other attribute values by the attribute information transformation part 22 and the knowledge database 10a is searched by the help information search part 15 according to these changed attribute values.

The attribute information transformation part 22 is effectuated by the execution of an attribute information transformation program by CPU 9. When a help information display request is received from the input device 8, the help information search part 15 requests attribute information from the attribute information transformation part 22. When the attribute information transformation part 22 receives this request, it acquires the program execution status 11a, the apparatus control display status 11b and study information 11c. Next, when the attribute information transformation part 22 reads the information in the transformation rules database 10d stored in HDD 10, it transforms the attribute information on the basis of these transformation rules and sends this to help information search part 15. Help information search part 15 searches for the attribute information in the knowledge database, based on the changed program execution status 11a, the apparatus control display status 11b and study information 11c and displays the help information file corresponding to the attribute information found by this search in the display 5.

FIG. 15 shows one example of the transformation rules database 10d according to an embodiment of the invention. The transformation rules database 10d puts the condition expression with the old attribute value in correspondence with the values of the new attribute values when this condition expression applies and stores these. For example, when the attribute information input to the attribute information transformation part 22 meets the condition 'the attribute information is that the program name is distance measurement and the region name is the heart', the program name is changed to 'heart distance measurement' and this is sent to the help information search part 15. For anything not defined by a new attribute value, a value that is identical to the old attribute value may be sent to the help information search part 15.

Another example of a transformation may be one in which a new attribute value is added when it matches the transformation rules and help information different from before is displayed based on this updated attribute value. For example, the previous help information may displayed under the conditions that the study region=abdomen, imaging mode=B mode, program name=distance measurement and screen division=divided into two. In this case, if there is a match at the attribute information transformation part 22 with the conditions that study region=abdomen, imaging mode=B mode, program name=distance measurement and screen division=divided into two; the new attribute value (attribute value Z=ACTIVE ) is added. By establishing a setting that help information B is displayed when attribute value Z=ACTIVE in the knowledge database 11a, it is possible to display help information that is different from before. By using the attribute transformation function in this way, it is easily possible to achieve the additional improvement that the optimum help information is extracted from the knowledge database 11a, In the examples described above, the attribute information that is input is changed during the attribute information transformation part 22 but the same function may be effectuated by transformation the knowledge database 10a based on the attribute information transformation rules, and then performing a search of the help information file based on this changed knowledge database.

In this fourth embodiment, as the knowledge database 11a searches for attribute information based on the transformation rules for attribute information, maintenance of the help information is easy, with no need to correct the attribute information accretions one by one.

Computer and System

The source of image data may be any appropriate image acquisition device such as an X-ray machine, CT apparatus, and MRI apparatus. Further, the acquired data may be digitized if not already in digital form. Alternatively, the source of image data being obtained and processed may be a memory storing data produced by an image acquisition device, and the memory may be local or remote, in which case a data communication network, such as PACS (Picture Archiving Computer System), can be used to access the image data for processing according to the present invention.

This invention conveniently may be implemented using a conventional general purpose computer or micro-processor programmed according to the teachings of the present invention, as will be apparent to those skilled in the computer art. Appropriate software may readily be prepared by programmers of ordinary skill based on the teachings of the present disclosure, as ill be apparent to those skilled in the software art.

A computer implements the method of the present invention, wherein the computer housing houses a motherboard which contains a CPU, memory (e.g., DRAM, ROM, EPROM, EEPROM, SRAM, SDRAM, and Flash RAM), and other optical special purpose logic devices (e.g., ASICS) or configurable logic devices (e.g., GAL and reprogrammable FPGA). The computer may also include plural input devices, (e.g., keyboard and mouse), and a display card for controlling a monitor. Additionally, the computer may include a floppy disk drive; other removable media devices (e.g. compact disc, tape, and removable magneto-optical media); and a hard disk or other fixed high density media drives, connected using an appropriate device bus (e.g., a SCSI bus, an Enhanced IDE bus, or an Ultra DMA bus). The computer may also include a compact disc reader, a compact disc reader/writer unit, or a compact disc jukebox, which may be connected to the same device bus or to another device bus.

As stated above, the system includes at least one computer readable medium. Examples of computer readable media are compact discs, hard disks, floppy disks, tape, magneto-optical disks, PROMS (e.g., EPROM, EEPROM, Flash EPROM), DRAM, SRAM, SDRAM, etc. Stored on any one or on a combination of computer readable media, the present invention includes software for controlling both the hardware of the computer and for enabling the computer to interact with a human user. Such software may include, but is not limited to, device drivers, operating systems and user applications, such as development tools. Computer program products of the present invention include any computer readable medium which stores computer program instructions (e.g. computer code devices) which when executed by a computer causes the computer to perform the method of the present invention. The computer code devices of the present invention can be any interpreted or executable code mechanism, including but not limited to, scripts, interpreters, dynamic link libraries, Java classes, and complete executable programs. Moreover, parts of the processing of the present invention may be distributed for better performance, reliability, and/or cost. For example, an outline or image may be selected on a first computer and sent to a second computer for remote diagnosis.

The invention may also be implemented by the preparation of application specific integrated circuits or by interconnecting an appropriate network of conventional component circuits, as will be readily apparent to those skilled in the art.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

Numerous modifications and variations of the present invention are possible in light of the above teachings. It is therefore to be understood that within the scope of the appended claims, the invention may be practiced otherwise than as specifically described herein.

What is claimed is:

1. An apparatus for medical diagnostic imaging, comprising:
   a first database configured to relate help information to a plurality of attribute values;
   an operations state acquisition part configured to acquire the attribute values, each of which expresses an aspect of a current operational status of the medical diagnostic imaging apparatus, wherein the current operational status includes information that specifies a program being run by an operator;
   a search part configured to search the first database, based on the attribute values and generates search result; and
   a display configured to display at least a portion of the help information based on the search results.

2. The apparatus of claim 1, wherein the portion of the help information includes at least one of clinical information for a study region, information on exemplary clinical images, and information relating to at least one caution for the study.

3. The apparatus of claim 1, wherein the current operational status includes information concerning a display form of the image.

4. The apparatus of claim 1, wherein the current operational status comprises at least one of an ultrasonic scan transmission frequency, an imaging mode, a position of focus point, a gain, and a type of probe in an ultrasound diagnostic apparatus.

5. The apparatus of claim 1, wherein the program includes at least one of a patient registration program, an annotation program, a program configured to display at least one body mark, an image file management program, and a measurement program configured to measure values from an image.

6. The apparatus of claim 1, wherein the search part is configured to search the database based on a plurality of attribute values that express study information.

7. The apparatus of claim 6, wherein the study information includes at least one of a study name, a study region, a disease name, a patient name, a doctor name, and a pharmaceutical product used for the study.

8. The apparatus of claim 1, further comprising:
   a second database configured to store at least one study sequence that defines a workflow of multiple tasks; and
   a workflow execution part configured to switch the current operational status of the apparatus successively according to the workflow,
   wherein the search part is configured to search the first database based on information about the workflow.

9. The apparatus of claim 8, further comprising:
   an analysis part configured to find at least one analysis value determined by an order of the multiple tasks in the workflow,
   wherein the search part is configured to search the first database, based on the at least one analysis value.

10. An apparatus for medical diagnostic imaging, comprising:
    a knowledge database configured to store help information associated with scan setting information and body region information;
    an operational state acquisition part configured to acquire the scan setting information and the body region information;
    a search part configured to search the knowledge database based on the scan setting information and the body region information and to generate at least one search result; and
    a display configured to display at least a portion of the help information based on the at least one search result.

11. A method for controlling a medical diagnostic imaging system, comprising:
    obtaining plurality of attribute values that express a current operational status of an apparatus for medical diagnostic imaging;
    searching knowledge database configured to store help information related to the operational status based on the plurality of attribute values and generating at least one search result; and
    displaying at least a portion of the help information based on the at least one search result.

12. A method for controlling a medical diagnostic imaging system, comprising:
    obtaining can setting information and body region information for an apparatus for medical diagnostic imaging;
    searching knowledge database configured to store help information based on the scan setting information and the body region information, thereby obtaining at least one search result; and displaying at least a portion of help information based on the at least one search result.

13. A computer readable medium on which is stored a computer program for controlling a medical diagnostic imaging system, said computer program comprising the steps of:

obtaining scan setting information and body region information for an apparatus for medical diagnostic imaging;

searching a knowledge database configured to store help information based on the scan setting information and the body region information, thereby generating at least one search result; and displaying at least a portion of help information based on the at least one search result.

* * * * *